United States Patent
Cascio et al.

[11] Patent Number: 5,180,053
[45] Date of Patent: Jan. 19, 1993

[54] CANTILEVERED NEEDLE PARK

[75] Inventors: Jack Cascio, Bridgewater; Konstantin Ivanov, Dunellen; Marvin Alpern, Glen Ridge, all of N.J.; Robert Cerwin, Pipersville, Pa.; Joseph Siernos, Whitehouse Station, N.J.

[73] Assignee: Ethicon, Inc., Somerville, N.J.

[21] Appl. No.: 843,138

[22] Filed: Feb. 28, 1992

[51] Int. Cl.⁵ .............................................. A61B 17/06
[52] U.S. Cl. ..................................... 206/63.3; 206/380
[58] Field of Search ................................ 206/63.3, 380

[56] References Cited

U.S. PATENT DOCUMENTS

| | | | |
|---|---|---|---|
| 4,424,898 | 1/1984 | Thyen et al. | 206/63.3 |
| 4,699,271 | 10/1987 | Lincoln et al. | 206/63.3 |
| 4,961,498 | 10/1990 | Kalinski et al. | 206/339 |
| 4,967,902 | 11/1990 | Sobel et al. | 206/63.3 |
| 5,131,533 | 7/1992 | Alpern | 206/63.3 |

FOREIGN PATENT DOCUMENTS 2618662  4/1976  Fed. Rep. of Germany ..... 206/63.3

Primary Examiner—William I. Price
Attorney, Agent, or Firm—James Riesenfeld

[57] ABSTRACT

A needle park for a package that holds one or more surgical needles and sutures has a generally planar base. A cantilevered arm, fixed at one end and free at its other end, extends above and parallel to the base. A needle is introduced between the free end of the arm and the base and held between the arm and base. A nib that extends from the free end of the arm toward the base secures the needle. The needle park may be molded as part of a one-piece needle and suture package and is well adapted for automatic loading.

11 Claims, 3 Drawing Sheets

CANTILEVERED NEEDLE PARK

BACKGROUND OF THE INVENTION

1. Field of the Invention

This invention relates to a needle park for securing needles, and, more particularly, to a needle park for a package that holds one or more surgical needles and sutures.

2. Description of the Related Art

Packages for surgical needles and sutures must, among other things, securely anchor the needles, yet permit them to be easily removed when they are to be used. A simple holder device (i.e., needle park) for accomplishing that consists of a foam strip adhered to the base of the package. The needle either pierces the foam or is inserted into a slit cut into the foam. A disadvantage of the foam strip is that it is a separate element from the rest of the package and must be adhered to the base of the package, requiring an additional operation during package manufacture.

U.S. Pat. No. 4,699,271, issued Oct. 13, 1987, to Lincoln et al. discloses alternate needle parks that hold needles in plastic clips or in pairs of slots cut into parallel walls.

U.S. Pat. No. 4,961,498, issued Oct. 9, 1990, to Kalinski et al. discloses an alternate needle park comprising a molded post and adjacent molded rail, which may both be formed on the floor of a suture package. The post and rail are separated by a distance that is slightly smaller than the diameter of a needle to be held. When the needle is placed between the post and rail, the rail flexes slightly, and the needle is held in place by contact on either side of the needle with the post and the rail. This design is limited to holding needles of a single diameter.

A somewhat similar needle park, which can hold a narrow range of needle diameters, is disclosed in U.S. Pat. No. 4,424,898. A needle park adapted to hold needles having a broad range of diameters, also disclosed in that patent, consists of a raised platform that has two string-like lengths arrayed parallel to each other, with their ends affixed to the platform. The strings have notched undersides and the platform is open below the strings. Needles are parked by insertion on top of the platform and under the strings. The notches on the strings prevent the needles from sliding along the length of the strings. This type of park can retain needles having a range of diameters; however, it depends on the flexibility of the strings and is not as simple or inexpensive to manufacture as are other needle parks.

U.S. Pat. No. 4,967,902, issued Nov. 6, 1990 to Sobel et al. discloses another type of needle park, comprising a wall that extends upward from the base of a needle package and that is interrupted by a gap into which the needle may be inserted. That type of park can only hold a needle whose diameter is substantially the same as the width of the gap between the wall ends. To increase the range of needle diameters that can be held, the wall ends can be undercut near the base and the base beneath the gap can be removed, which permits the wall ends to flex and bend, thereby accommodating a somewhat wider range of needle diameters. The range of needle diameters that can be held securely is limited, however.

A drawback that these earlier needle parks all have in common to a greater or lesser degree is that they are not adapted for one-piece manufacture and/or are not well adapted to simple, automated loading of a needle in the park. Instead, they generally require a separate needle park element that must be mounted into the package, or rather careful and precise needle placement, or both. Thus, if loading the needles into the packages is included as a manufacturing step, all the prior art needle parks suffer from certain manufacturing drawbacks.

SUMMARY OF THE INVENTION

In accordance with the present invention, a needle park for securing a needle comprises:

a generally planar base, an elongated arm that, having a first end secured in a fixed relationship to the base and a second end that is free, extends in a direction generally parallel to the base, and a nib that extends toward the base from a point near the free end of the arm.

The needle park of the present invention is adapted for being molded as part of a needle and suture package, which permits the packages to be made simply and inexpensively. At the same time, a single park can hold securely a needle whose diameter may vary over a broad range. Finally, the needle park is well adapted for automated loading.

DETAILED DESCRIPTION OF THE INVENTION

The needle park of the present invention is adapted to securely anchor a surgical needle whose diameter is anywhere within a broad range of diameters. The needle park is typically part of a needle and suture package, and it does not unduly interfere with removal of the needle from the package. At the same time, the needle park is economical to manufacture, including the step of loading the needle. Thus, a suture package using this needle park can be manufactured by molding, stamping, or thermoforming of thermoplastic materials, followed by automated needle (and suture) loading.

Figure 1:
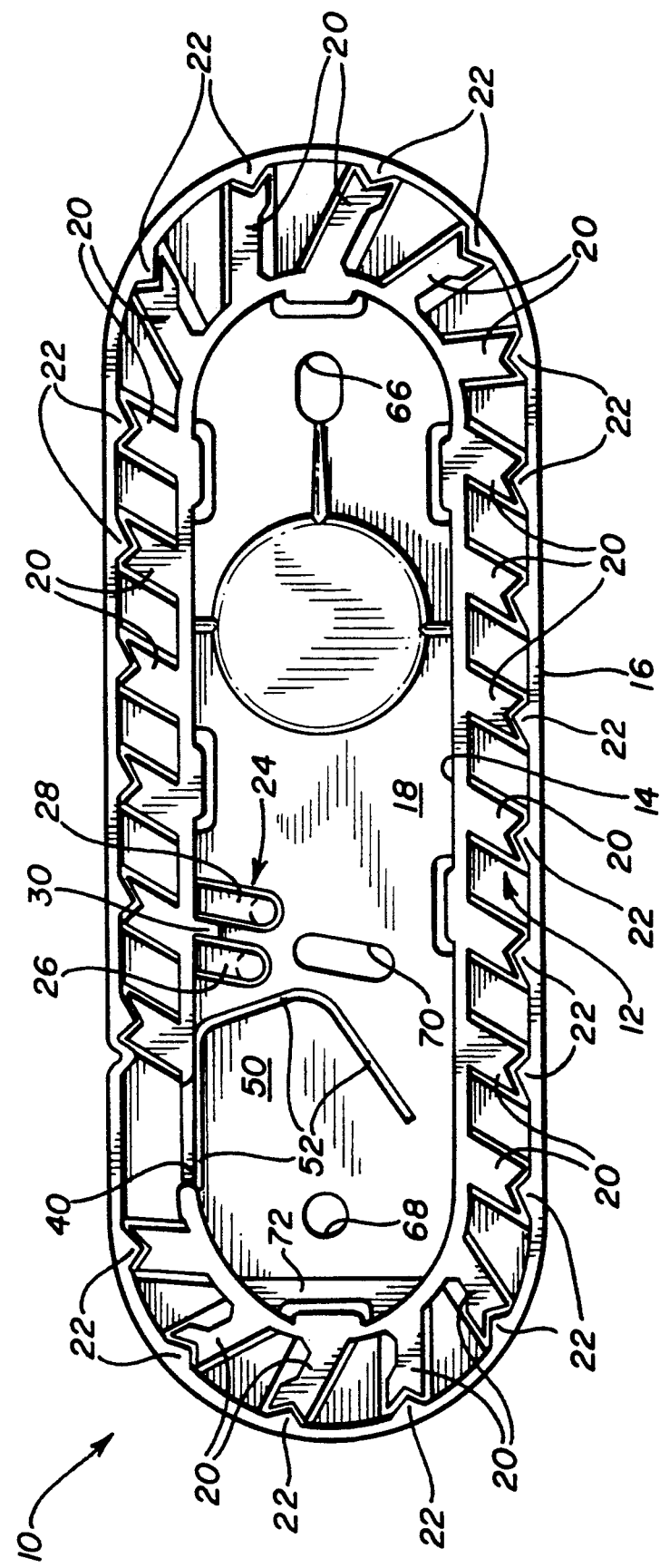
FIG. 1 is a plan view of a surgical needle and suture package of the present invention.

FIG. 1 is a plan view of a one-piece needle and suture package of the present invention. The package 10 includes a central floor area 18 which is surrounded by an outer oval channel 12 having two opposing straight sections connected by two semicircular end sections. The channel, for containing a suture, is defined by inner wall 14 and outer wall 16, which extend upwardly from the floor 18.

To prevent the suture from lifting up out of the channel, cantilevered fingers 20 extend from the top of inner wall 14 most of the way across channel 12. Nibs 22, one for each finger 20, extend from outer wall 16, to leave a small gap between each finger and the corresponding nib.

Needle park 24 comprises cantilevered arms 26 and 28, which extend horizontally from wall 14, above the base, and optional wall, or "stop," 30. The elevation of arms 26 and 28 above the base and their mechanical properties are chosen to permit them to hold needles of the desired range of gauges. Nibs 32 and 34 at the ends of arms 26 and 28, respectively, capture needle 2. Adjacent to needle park 24, is an optional flap 50, defined by cutout 52. The height of inner wall 14 is reduced (or the wall is eliminated) along part of its length to form opening 40, through which the suture can pass into channel 12. A single needle park is shown in the package of FIG. 1; however, multiple needle parks may be used in a package intended to hold double-armed or multiple sutures.

In a preferred embodiment of the present package, three holes in the base are used during loading a needle and suture into the package. The package is supported on an assembly platform during the loading process by pins that extend upward through holes 66 and 68. Thus supported, a needle is placed on the base near needle park 24 and is then pushed into place near or against stop 30 by an "L" shaped bar that extends up through hole 70. Note that this (preferred) needle-loading method does not require that the needle be precisely positioned on the base, before it is pushed into place. The attached suture is then looped about the pin that extends through hole 68 and passed through opening 40 into channel 12. The suture is wound into channel 12 by successively raising the free end of each finger 20 just before the suture is placed and permitting the finger to spring back into place immediately thereafter.

The package design preferably provides close spacing of the fingers so that the end or "tail" of the suture is likewise contained in the channel.

When winding is complete, the pins are withdrawn from holes 66 and 68 and a paper cover (not shown) is placed over the package.

Figure 2:
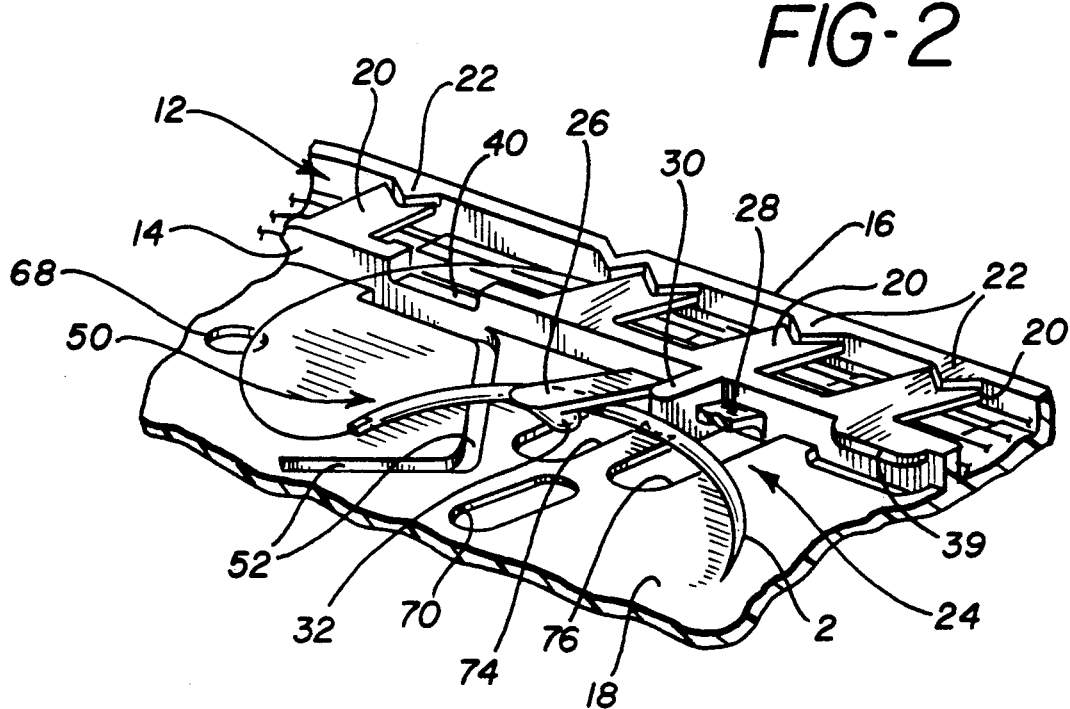
FIG. 2 is an isometric view of a needle park of the present invention.

FIG. 2 depicts needle park 24, with curved needle 2 held against floor 18 by cantilevered arms 26 and 28 (partially cut away). Although depicted as curved, needle 2 could have substantially any shape, including straight. When needle 2 is to be removed. The user grasps the needle with a forceps. Since the needle is resting flush with the floor of the package, making it difficult to securely grasp the needle with the tip of the forceps, the relief flap 50 is preferably provided. As the user presses the tip of the forceps against the relief flap, the flap gives way and bends away from the needle, thereby enabling the user to pass the tip of the forceps beyond the needle. The needle may then be securely grasped in the tip of the forceps and removed from the needle holder. Optional stop 30 keeps the needle away from wall 14 to facilitate grasping the needle. Inclined floor section 72 facilitates removing the needle from the package without hangup.

Figure 3:
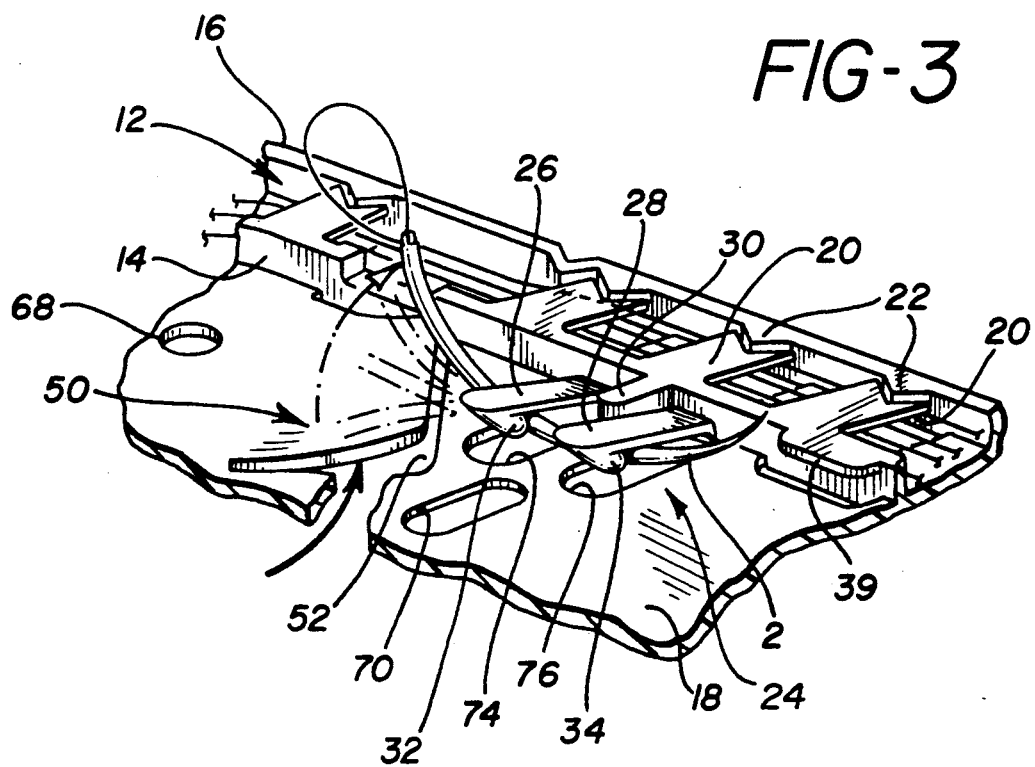
FIG. 3 illustrates a needle-removing mechanism.

Flap 50 also provides a means to grasp the needle in another way. If the cover has been removed, then the ends of the needle can be rotated into an upright position simply by pushing against the underside of flap 50 (as shown in FIG. 3). The needle can then be easily grasped by forceps or fingers.

Package 10, including needle park 24, may be fabricated from any of a number of materials; however, molded thermoplastics are preferred, because they permit low cost and high precision. If package 10 is to be molded in one piece, then holes 74 and 76 are needed, on base 18 opposite arms 26 and 28, respectively.

Figure 4:
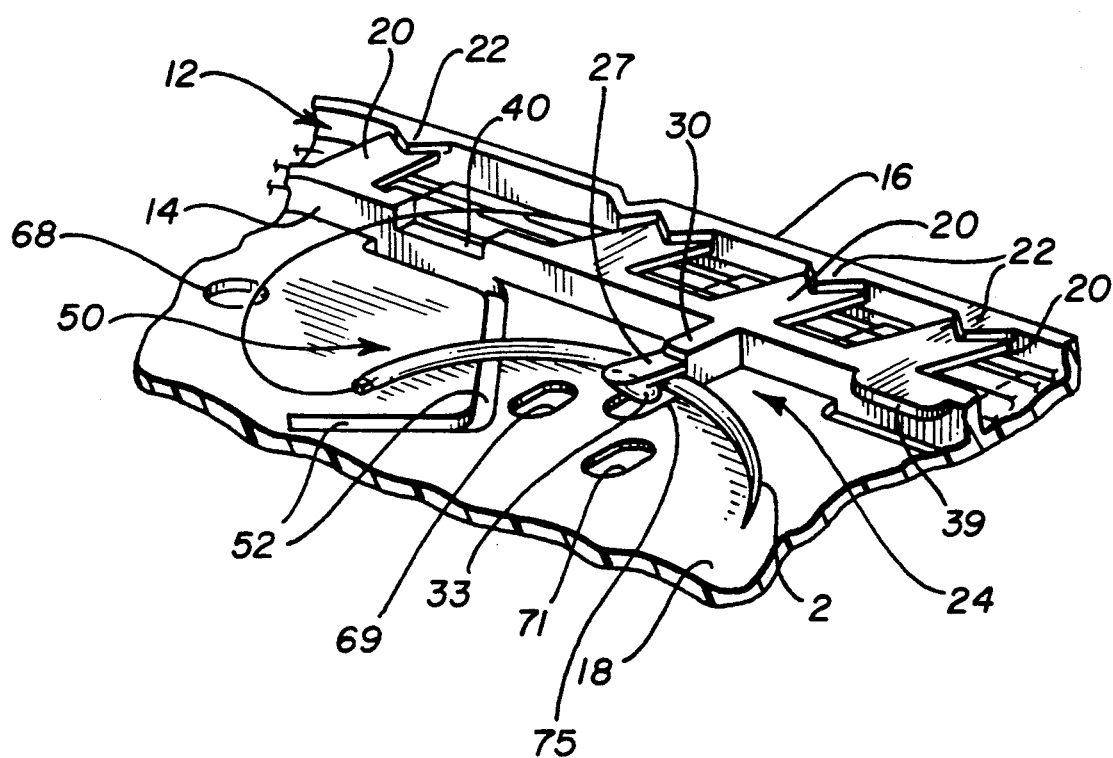
FIG. 4 is an isometric view of an alternative needle park embodiment.

FIG. 4 depicts an alternative embodiment of a needle park that has but one cantilevered arm 27 with nib 33 to hold needle 2. If the package is to be molded, then hole 75 is needed on base 18 opposite arm 27. To facilitate loading needle 2 into needle park 24, elongated holes 69 and 71 in base 18 permit "L" shaped bars to extend up through the base and push the needle toward stop 30.

We claim:
1. A needle park for securing a needle, comprising
a generally planar base,
an elongated arm that, having a first end secured in a fixed relationship to the base and a second end that is free, extends in a direction generally parallel to the base, and
a nib that extends toward the base from a point near the free end of the arm.

2. The needle park of claim 1 further comprising a second elongated arm that extends in a direction generally parallel to the base and that is separated from the base by substantially the same distance as the first arm, the second arm having a secured first end spaced apart from the secured first end of the first arm and a free second end spaced apart from the free second end of the first arm.

3. The needle park of claim 2 further comprising a first wall generally perpendicular to the base for securing the first ends of the first and second arms.

4. The needle park of claim 3 further comprising a second wall, secured at one end to the first wall, and extending from the first wall between the first and second arms.

5. A package for a needle and suture comprising the needle park of claim 1.

6. The package of claim 5 in which the base has a plurality of elongated holes whose long dimensions are generally parallel to each other and to a projection of the elongated arm onto the base.

7. A package for a needle and suture comprising the needle park of claim 2.

8. The package of claim 7 in which the package is fabricated from a thermoplastic material.

9. The package of claim 8 in which the base is cut away in the regions opposite the arms.

10. The package of claim 7 in which the base has an elongated hole that extends generally parallel to and between projections of the first and second arms onto the base.

11. The package of claim 7 in which the base has a cutout section that defines a flexible flap which can be tilted toward and away from the arms.

* * * * *